United States Patent [19]

Freedland

[11] Patent Number: 4,632,101
[45] Date of Patent: Dec. 30, 1986

[54] ORTHOPEDIC FASTENER

[76] Inventor: Yosef Freedland, 11871 Artesia Blvd., Artesia, Calif. 90701

[21] Appl. No.: 696,991

[22] Filed: Jan. 31, 1985

[51] Int. Cl.$^4$ ............................................... A61F 5/04
[52] U.S. Cl. ............................ 128/92 YW; 128/92 YY
[58] Field of Search ............ 128/92 BC, 92 BA, 92 B, 128/92 R

[56] References Cited

U.S. PATENT DOCUMENTS

| | | | |
|---|---|---|---|
| 1,269,912 | 6/1918 | Dunham | 128/92 B |
| 3,759,257 | 9/1973 | Fischer et al. | 128/92 BC |
| 3,760,802 | 9/1973 | Fischer et al. | 128/92 BC |
| 3,779,239 | 12/1973 | Fischer et al. | 128/92 BC |
| 4,091,806 | 5/1978 | Aginsky | 128/92 BC |
| 4,204,531 | 5/1980 | Aginsky | 128/92 BC |
| 4,227,518 | 10/1980 | Aginsky | 128/92 BC |
| 4,236,512 | 12/1980 | Aginsky | 128/92 BA |
| 4,275,717 | 6/1981 | Bolesky | 128/92 BA |
| 4,409,974 | 10/1983 | Freedland | 128/92 BC |
| 4,519,100 | 5/1985 | Wills et al. | 128/92 BA |

Primary Examiner—Robert P. Swiatek
Assistant Examiner—C. W. Shedd
Attorney, Agent, or Firm—Georges A. Maxwell

[57] ABSTRACT

An orthopedic implant device is provided for bringing portions of a fractured bone into proper alignment and abutment. The device is an elongate generally cylindrical unit surgically implanted within living bone with a fractured portion and includes a plurality of pivotally mounted struts which are deployed within the cancellous material of the bone distant from said fractured portion thereof. The struts are pivotally deployed radially outwardly until anchoring contact with the interior surface of the surrounding cortex of the distant portion of the fractured bone is established. The components of the device maintain a force urging the portions of the bone defining the fracture toward each other. When the device is to be removed from the bone, the struts can be collapsed so that the device can be withdrawn. Should regrowth of bone and the anchoring interaction between the struts and the bone prevent the struts from collapsing, the struts can be severed from the device and withdrawn by elongate flexible connectors which are connected with and extend between the struts and the remaining structure of the device.

16 Claims, 12 Drawing Figures

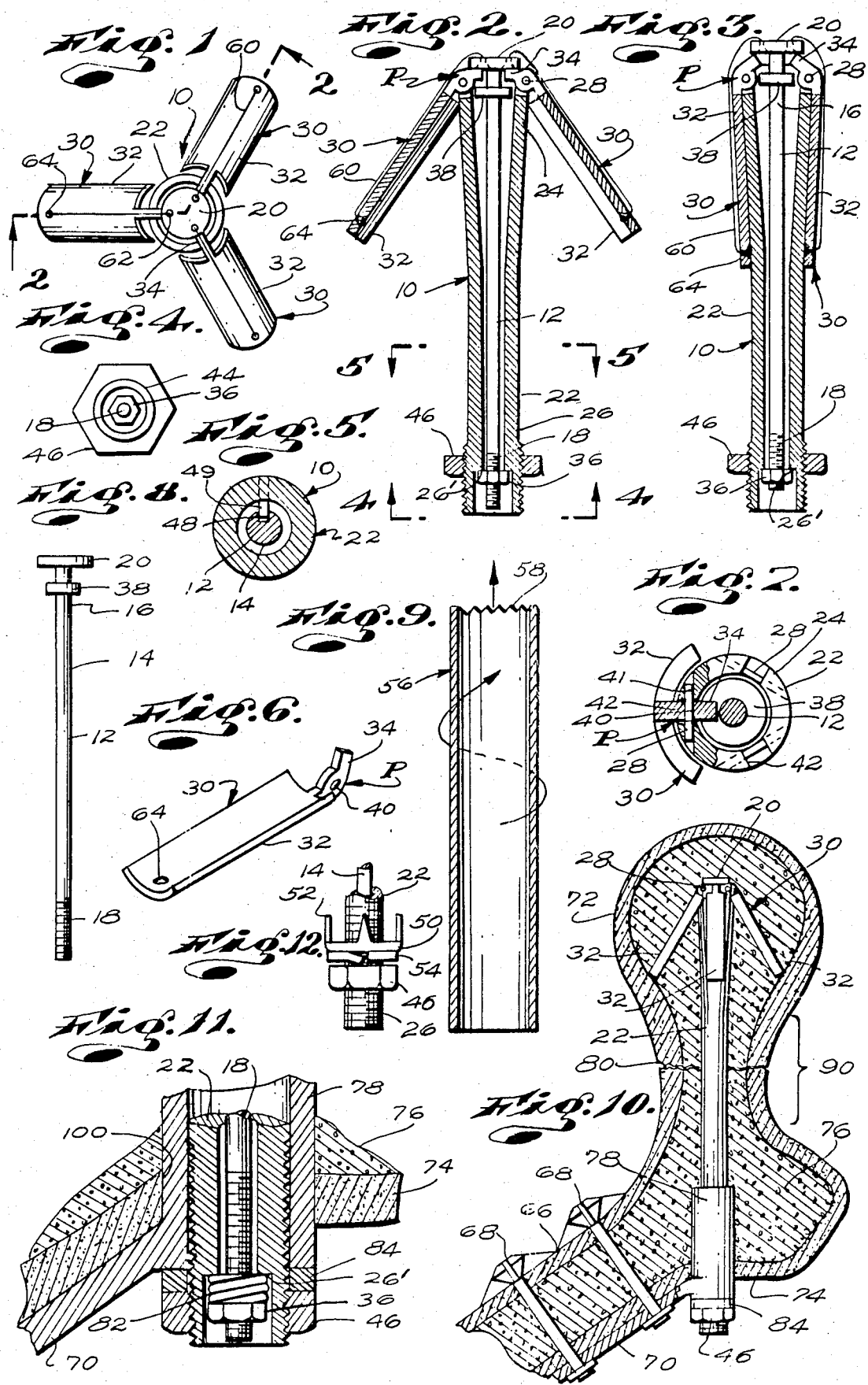

ORTHOPEDIC FASTENER

BACKGROUND OF THE INVENTION

The present invention relates to surgical implant devices, especially implant devices utilized in procedures where rigid internal fixation of bone portions is desired.

Various orthopedic pins and fasteners have been devised to aid in properly fixating bones or bone portions so as to promote as much as possible the primary healing of fractured bones to their original condition. The most common devices used to attain fixation of portions of fractured bones include and rely upon screw fasteners which must be entered and advanced into the bone structures worked upon. Newer devices which have not yet gained wide acceptance provide elongate fasteners which are of relatively narrow configuration when inserted into bone being worked upon and which operate to expand laterally or radially after being inserted to attain fixation in the bone. These devices are commonly classified or called "expanding nail devices".

Both the above noted screw type devices and expanding nail type devices are deficient in several important respects. To comprehend the nature of the deficiencies of these prior art devices, the structural characteristics of living bone must be considered.

Living bones are formed of cancellous material within a surrounding cortex. The compressive strength of compact cortical bone is 10,000 to 35,000 pounds per square inch while shear strength is considerably less. The cortex encases the much softer spongly cancellous bone which yields under very small pressures.

In the case of common screw type devices, such as "sliding bone screws" used in the hip, the devices are placed in bone being worked upon by drilling holes though the cortex of the trochanter region and through the cancellous material thereof across the area of fracture and into the cancellous material of the femoral head of the bone. The only forces compressing the proximal and distal portions or opposite portions of the fractured bone are provided by the threads of the screws gripping into the cancellous bone of the femoral head and the ends of the screws (and related plates) acting against the cortex of the femur. Since the cancellous bone of the head is a yielding, spongy material, very little compressive or fixative force is provided by a conventional screw-type device or "sliding bone screw".

The expanding nail type devices were devised to provide fixation devices which more effectively fixate the portions of fractured bones to promote proper healing. One such device is described in my U.S. Pat. No. 4,409,974. The device which is the subject matter of my above noted patent is an implant device characterized by a tubular member having a frustoconical head and a plurality of traingular shaped arms. That implant device is inserted into a bore in the bone worked upon, across the fracture in said bone, with the arms in a radially inwardly folded or collapsed position. Once inserted, tension is exerted on trailing lines emanating from an opening in the tubular member remote from the head thereon. By pulling the lines, the arms are pivoted or rotated from said folded position to radially outwardly disposed anchoring positions within the cancellous material of the bone. That implant device can be collapsed for removal or for repositioning by folding the arms back or radially inwardly. This is accomplished by pulling a generally cylindrical mesh sleeve disposed about the tubular member and connected with the arms by filament, longitudinally of the tubular member.

One distinct advantage of my above noted patented device over prior art screw type and expanding nail type devices resides in the fact that the arms, when deployed or disposed radially outwardly, provide fixation through compressive forces on the bone to reduce fractures and to fixate bone portions, whereas common screw type devices rely on "shear cylinder" forces applied directly onto and through the bone. Also, the nature of my above noted patented device is such that by increasing the cross-section of the arms, the surface area of the arms acting in the material of the bone is increased and notably greater forces can be applied onto and through the bone worked upon, without weakening it. In the case of screw type devices, to generate greater forces the screws must be made greater in diameter. Such increases in the diameter of screws requires that the diameter of the bores or openings established in the bone to receive the screws must be increased accordingly, intrinsically weakening the bone, especially upon removal of the devices.

My above noted patented device had many design advantages over prior art expanding nail type devices. As many of those design advantages have been incorporated into my new device which is the subject matter of the present invention, comparison of the prior art and my present invention will be set forth in the following description of a preferred embodiment of my present invention.

DESCRIPTION OF THE INVENTION

The present invention is a surgical implant device for fixating bones and bone portions in a living body. The device includes a central shaft having an elongate shank with inner deployment and outer securement ends. A lever actuating means, in the form of an annular flange, is related to the inner deployment end of the shank. An elongate tubular sleeve is slidably engaged about the shank of the shaft and has inner deployment and outer securement ends. A plurality of pivotal axes formed by pivot pins are arranged about the inner deployment end of the sleeve. The pivotal axes are spaced circumferentially about and radially offset from the central axis of the sleeve about the inner deployment end thereof. A plurality of rigid anchor arms in the form of cranks are pivotally mounted on and about the inner deployment end of the sleeve about said pivotal axes.

Each crank-like anchoring arm has a short normally substantially radially inwardly projecting operating lever which is engaged by the lever actuating means on the shaft and has an outer elongate strut. The anchoring arms are rotatable about the pivot pins defining said pivotal axes, which pins serve as fulcrums. The struts can thereby be moved from normally collapsed positions of longitudinal orientation where they occur substantially parallel with and adjacent to the exterior of the sleeve to deployed radially outward orientation where they are out of parallel with and project substantially radially and longitudinally outwardly relative to the axis of the sleeve. Pivotal movement of the arms is achieved by the lever actuating means acting upon the levers of the arms. A suitable fastening means is provided for holding the shaft and sleeve at a selected position of relative longitudinal placement to maintain the struts of said arms in desired or set radially outward orientation or deployed position. The noted fastening means also serves to maintain the shaft in tension and the sleeve in compression.

The manner of deployment and the configuration of the struts of the arms provide several unique advantages over those expanding nail type devices provided by the prior art, for both femoral shaft and head fixation. Specifically, the design and construction of the device allows the struts of the arms to be constructed with greater width and length and in a greater number of different shapes than can the arms of prior art expanding nail type devices be made. The reason for this is because the anchoring arms of prior art devices are deployed in such a way that they must be resilient and flexible and such that they will conform to the interior surfaces of related bone. This resilience and flexibility limits the allowed cross-sectional area of the arms as well as their length and shape. Further, the material from which the resilient and flexible arms of prior art devices can be made is limited whereas the arms of the present invention can be made of a far greater variety of materials. In certain expanding nail-type devices provided by the prior art, the arms are stored within outer encasement or sleeve-like parts with slots or openings through which the arms are deployed. In such devices, no more than two arms can be provided. The two arms in such device must be flat and can be no greater in thickness than one-half the internal diameter of their related encasing parts. The length and width of the arms in such prior art devices are similarly limited.

In the case of my present invention, the number, size and shape of the struts is not limited by an encasing part or the like and the number, size and shape of those struts can be varied greatly, as desired and as circumstances require.

Furthermore, when the struts of the arms of the present invention are deployed and in said radial outward orientation, they do not extend perpendicular to the shaft and sleeve, but rather, are inclined radially and longitudinally outwardly at an angle back or outward from the deployment ends and toward the securement ends of the shaft and sleeve. This dispositioning of the struts allows the outer or free ends of the struts to establish firm seated or anchoring contact with the inner surface of the cortex of long bones of the human body. Specifically, in the case of a fracture of the neck in the femur of a patient, the struts of my new implant device, when deployed, establish firm, seated or anchoring contact with the strong, cortical structure of the femural head as it attaches to the neck of the bone. In the femoral shaft, the struts contact the cortex of the condyles at their flair from the shaft.

The implant device of the present invention has the further advantage of providing a larger compressive force pressing the bone portions together on either side of a fracture than can be attained with prior art devices. The attaining of such greater compressive forces is made possible by the manner in which the struts can be set to firmly seat or anchor against the bone cortex and exert large compressive forces thereagainst in a substantially axial direction with only a relatively small radial component of force. In contrast, some prior art devices employ the principle of a wedge to drive anchoring arms radially outward from an axle shaft. In such an arrangement, the arms exert a large lateral or radial force on a large area of the walls of the medulla. It is quite possible that if the shaft or neck of a bone is weakened in the area where force is applied by such devices, due either to undiagnosed secondary hairline fractures, osteoporosis, or improper reaming of the bore in which the fastener is deployed, further fracturing and displacement of bone fragments is likely to occur. The struts of the anchoring arms of the present invention, on the other hand, act within the short span of the femoral head or femoral condyles and primarily in an axial rather than a radial direction.

A further advantage of the present invention is that deployment of the struts of the anchoring arms does not require advancement of a deloying element along a threaded shaft in order to effectuate deployment of the struts. Such worm screw mechanisms are utilized in many prior art expanding nail type devices. However, due to the healing process, conventional screw mechanisms tend to become pocked and pitted due to normal physiologic conditions in vivo. They therefore may not function properly to fold or collapse arms or struts radially inward when the implant devices are to be removed. Removal of such devices may be impossible to achieve without considerable damage or destruction of the bone and which is likely to cause further complications for the patient.

A further and very significant advantage of the present invention is the provision of a positive mechanism for collapsing the anchoring arms without the necessity of a screw mechanism to move or fold the struts inwardly and against the sleeve of the device and to thereby allow substantially free withdrawal of the device from the bone. A further highly significant feature of my invention is the provision of alternate means for effectuating removal of the device. In some cases the regrowth of the bone around the implant device might prevent reverse operation of the deployment means and radial inward movement of the struts from their deployed positions to their normal positions adjacent the sleeve of the device. In such situations, if the struts cannot be otherwise "released", the device could not be withdrawn without causing considerable damage to the structure of the bone. In accordance with the foregoing and in furtherance of my invention, removal of the implant device does not depend entirely upon proper reverse operation of the deployment means. In my new implant device, elongate flexible connectors in the form of filament cables are connected with and extend between the outer free end portions of the struts and the shaft. If the struts cannot be pivoted and moved radially inwardly from their deployed to their collapsed positions against the sleeve by longitudinal movement of the shaft relative to the sleeve, a tubular cutting tool is slidably engaged about the sleeve and is rotated to cut or saw through the inner ends of the struts, adjacent the exterior surface of the sleeve. Following severance of the strut in the manner set forth above, the shaft and sleeve assembly can be withdrawn from the bone and the severed struts are thereafter drawn free and pulled from the bone by the flexible connectors.

My present invention embodies and can be described as a method of in vivo fixation of proximal and distal portions of a fractured living bone formed of cancellous material within a surrounding cortex. According to the method of my invention, an opening or bore is drilled or otherwise defined through the cortex of the proximal bone portion and into the cancellous material of the near and distant bone portions. An implant device is inserted into the bore. The device is formed of an elongate shaft having a shank with inner deployment and outer securement ends and a flange-like deployment means at its inner deployment end. An elongate tubular sleeve is slidably engaged about the shaft and has inner deployment and outer securement ends. Pivot means are provided at the inner deployment end of the sleeve and define a plurality of circumferentially spaced axes of rotation radially outwardly offset from the axes of the shaft and sleeve. A plurality of crank like arms are mounted about said axes for pivotal movement relative to the shaft and sleeve. Each arm has a radially outward strut and a radially inward operating lever angularly related to the strut and engaged by said deployment means. Fastening means are provided at the outer securement ends of the shaft and sleeve. Once the implant device has been inserted into the bore formed in the bone, the shaft is shifted axially outwardly relative to the sleeve to apply force through the deployment means onto the levers of the arms to rotate them. Upon rotation of the arms, the struts are pivoted radially outward from normal collapsed positions adjacent to the sleeve to deployed positions where they extend radially and longitudinally outward from the sleeve and establish anchoring engagement within the cancellous material of the bone and with the interior of the cortex of the bone in the distal bone portion. The shaft is then placed in tension and the sleeve is placed in compression so as to maintain the struts in their noted deployed position. The outer sleeve is then suitably secured to the outer cortex of the bone and the sleeve is put in tension. This draws the proximal and distal portions of the fractured bone toward each other. The distal portion of the bone is thereby continuously pressed toward the proximal bone portion, thereby promoting rapid and proper healing of the bone fracture.

Where difficulties are encountered in subsequent removal of the implant device due to regrowth of the bone structure about the struts, an elongate tubular cutting tool is slidably and rotatably engaged about the sleeve and is moved longitudinally inwardly and is rotated to engage and to cut the struts from the remainder of the structure of the device. The cutting tool, sleeve and shaft are thereafter withdrawn from the bone and the struts are thereafter pulled free and withdrawn from the bone by exerting tension on elongate flexible connectors or cables which are joined to and extend between the outer free end portions of the struts and the shaft or sleeve. The provision of this alternate means for removing the implant device allows for independent removal of the shaft and sleeve assembly and of the several struts without destruction or adverse damage to the bone structure.

The foregoing will be fully understood from the following detailed description of one preferred form and embodiment of my invention, throughout which description reference is made to the accompanying drawings.

DESCRIPTION OF THE DRAWINGS

FIG. 1 is an inner end view of an implant device embodying my invention in which the struts are deployed;

FIG. 2 is a longitudinal sectional view taken substantially as indicated by line 2—2 on FIG. 1;

FIG. 3 is a view similar to FIG. 2 with parts in another position;

FIG. 4 is a view taken substantially as indicated by line 4—4 on FIG. 2;

FIG. 5 is a sectional view taken substantially as indicated by line 5—5 on FIG. 2;

FIG. 6 is a perspective view of an anchor arm;

FIG. 7 is an enlarged sectional view of a portion of the structure that I provide;

FIG. 8 is an elevational view of the shaft of my device;

FIG. 9 is a longitudinal sectional view of a cutting tool provided by my invention;

FIG. 10 is a sectional view showing the device in fixating relationship in a fractured femoral neck;

FIG. 11 is an enlarged sectional view of a portion of the structure shown in FIG. 10; and FIG. 12 is a view of an alternate means for securing the securement end of the device to a related bone.

DETAILED DESCRIPTION OF THE INVENTION

In FIGS. 1 through 8 of the drawings, I have illustrated a surgical implant device 10 embodying my invention and which is particularly designed and intended for in vivo implantation to fixate fractured living bone in the manner illustrated in FIG. 10 of the drawings. The implant device 10 includes an elongate shaft 12, an elongate tubular sleeve 22 and a plurality of rigid anchoring arms 30.

The shaft 12 has a shank 14 with inner deployment and outer securement end portions or ends 16 or 18. A generally disk-shaped deployment flange 20 projects radially from the shank 14 at the inner deployment end 16 thereof.

The tubular sleeve is an elongate part freely slidably engaged about the shank 14 ad has inner deployment and outer securement end portions or ends 24 and 26. The inner deployment end 24 of the sleeve 22 is formed to establish and to carry parts of a pivot means P. The pivot means P includes a plurality of circumferentially spaced, short axles or pivot pins 28 mounted in the wall of the sleeve and bridging vertically extending radial slots 42 formed in said sleeve and as shown in detail in FIG. 7 of the drawings. The pivot pins 28 are radially offset from and are spaced circumferentially about the axis of the shaft 12. The pins 28 are provided to pivotally mount the arms 30 for free rotation relative thereto and for pivotal movement relative to the shaft 12 and to the sleeve 22.

Each anchor arm 30 has an elongate strut 32 which occurs outside the sleeve 22. The strut 32 has a radial inner or base end and a radial outer or free end. In the case illustrated, the strut is generally arcuate in cross-section as shown in FIGS. 6 and 7 of the drawings. Each anchor arm also has a short lever arm 34 that is joined integrally with and is angularly related to the strut 32. The strut 32 on each arm is pivotally moveable from a normal or collapsed first position where it occurs adjacent to and extends longitudinally of the sleeve 22, as shown in FIGS. 3 and 7 of the drawings, to a radially disposed deployed second position where it extends radially outwardly and longitudinally outwardly from the sleeve 22, as shown in FIGS. 1 and 2 of the drawings. The anchor arms 30 and/or struts 32 thereof are deployed from that normal or first position shown in FIG. 3 of the drawings to that deployed or second position shown in FIG. 2 of the drawings by forces (movement) applied to the operating levers 34 by the deployment flange 20 on the shaft 12. Deployment of the arms in the manner noted above is effected by axial outward shifting of the shaft 12 and flange 20 relative to the sleeve 22, as illustrated in FIGS. 2 and 3 of the drawings.

A nut 36 is threadedly engaged on the outer securement end portion 18 of the shaft 12 and engages the outer securement end of the sleeve 22 as will hereinafter be described. The nut 36 serves as a fastening means for immobilizing or stopping the shaft 12 and the sleeve 22 when the shaft 12 has been shifted longitudinally relative to the sleeve to hold the struts 32 in deployed or radial disposition and to hold the shaft 12 in tension and the sleeve 22 in compression when the device is implanted.

As illustrated in FIG. 8 of the drawings, the shaft 12 is threaded at its outer securement end 18 and the deployment flange 20 is formed integrally therewith at its inner deployment end 16. The shaft 12 is also provided with a second radially outwardly projecting flange 38 spaced longitudinally outward from the flange 20 and defining a gap between said flanges, as best shown in FIG. 8 of the drawings. The operating levers 34 of the anchoring arms 30 extend into the gap to establish working bearing engagement with the flanges 20 and 38, as clearly shown in the drawings.

With the structure described above, it will be apparent that longitudinal outward movement of the shaft relative to the sleeve 20, from that position shown in FIG. 3 of the drawings to that position shown in FIG. 2 of the drawings, pivots the lever arms 34 downwardly and the struts 32 from their normal longitudinal orientation, shown in FIG. 3 of the drawings, to their deployed position, shown in FIG. 2 of the drawings. Movement of the shaft 12 in the opposite direction, that is, longitudinally inwardly relative to the sleeve 20, pivots the lever arms 34 upwardly and the struts 32 inwardly from their deployed position, as shown in FIG. 2 of the drawings to their normal or collapsed position shown in FIG. 3 of the drawings.

As shown in FIGS. 6 and 7 of the drawings, the struts 32 of the anchor arms 30 are arcuate in cross-section. As shown in FIG. 3 of the drawings, the struts 32 reside in juxtaposition and extend about adjacent portions of the sleeve 22 when they are in their normal or collapsed position.

As clearly shown in the drawings, the operating levers 34 are short tabs which are angularly related to the struts 32 at an angle of about 45°. The anchoring arms 30 are preferably formed as unitary parts cast or otherwise formed of some suitable material such as stainless steel or a rigid plastic.

Bores or pivot pin receiving openings 40 are formed through the arms 30 at the areas of joinder between the levers and struts thereof, which areas can and will be hereinafter referred to as the base portions of the lever arms with which the inner ends of the struts are joined.

The bores 40 in the base portions of the arms 30 rotatably accommodate the central portions of the pivot pins 28. The opposite end portions of the pivot pins 28 are engaged in aligned openings 41 in the wall of the sleeve 22. The operating levers 34 and struts 32 of the anchoring arms 30 rotate or pivot in the longitudinally and radially extending planes which pass through the axes of the sleeve and shaft. The base portions of the anchor arms 30 occur within the longitudinally extending radially and longitudinally opening slots 42 established in the inner deployment end portions of the sleeve and across which the central portions of the pivot pins 28 extend.

In the preferred carrying out of my invention and as shown in the drawings, the inner deployment end portion of the sleeve 22 is flaired longitudinally inwardly and radially outwardly to suitably increase the diametric extent of the inner deployment end of the sleeve and to better accommodate those parts of the device which are related thereto.

The outer securement ends 26 and 18 of the sleeve 22 and shank 14 of the shaft 12 are externally threaded. The outer securement end 26 of the sleeve 22 is counterbored and defines an internal, annular, axially outwardly disposed bearing seat 26'. The above noted nut 36 is threadedly engaged on the securement end 18 of the shaft 14 and bears longitudinally outwardly against the seat 26' in the sleeve 22 when the device 10 is implanted and set in a related bone.

A second, larger nut 46 is threadedly engaged on and about the exterior of the securement end 26 of the sleeve 22 and projects radially outwardly therefrom. The nut 46 directly or indirectly bears longitudinally inwardly relative to the longitudinal axis of the device against the outer surface of the cortex of a bone in which the device is implated so as to maintain the sleeve 22 in tension while the nut 36 maintains the shaft 12 in tension when the device is deployed to fixate portions of a fractured bone.

Preferably, some means is provided to prevent the shaft 12 from rotating relative to the sleeve 22. While this function may be performed by a number of different mechanical means or devices, that means which I have elected to illustrate includes an inwardly projecting key or tab 48 formed on the inner cylindrical surface of the sleeve 22 and slidably engaged in a longitudinally extending radially outwardly opening keyway or slot 49 formed in the shank 14 of the shaft 12. It will be apparent that the noted tab and slot allow for free relative axial shifting of the shaft and sleeve and prevent relative rotation thereof.

When using my device to fixate bones, such as the long shaft of the femur, without the provision and collateral use of a sleeve or bone plate, it is necessary to provide some means for immobilizing or preventing rotation of the sleeve 22 relative to the bone in which the device is deployed. To this end a flat annular washer 50 with longitudinally extending spikes 52, as clearly indicated by FIG. 12 of the drawings, can be advantageously used. The washer 50 is interposed btween the nut 46 and the outwardly disposed surface of the bone in which the device is installed, with the spikes 52 directed toward said surface of the bone. A lock washer 54 may also be employed to aid in preventing the sleeve from rotating relative to the nut 46 once the struts 32 of the arms 30 are deployed.

The nut 46 is first engaged with the threaded outer securement end 26 of the sleeve 22 so that the spikes 52 of the washer 50 establish contact with the cortical surface of the bone. Once the struts 32 of the arms 30 are fully deployed and in their radial disposition shown in FIG. 2 of the drawings, the nut 36 is tightened to place the shaft 12 in tension. Tightening the nut 36 causes the spikes 52 to embed in the cortical bone surface. The lock washer 52 exerts locking force on the nut 46 to prevent the sleeve from rotating as the nut 36 is tightened. Once the struts 32 of the arms 30 lodge against the inner surface of the bone cortex, as shown in FIG. 10 of the drawings, bone portions may tend to rotate the sleeve 22. However, by employing the spiked washer 50 and lock washer 54, such turning or torquing of the bone portions is suitably prevented while tensile force is exerted. The tensile force on the shaft 12 serves to draw the near and distant portions of the fractured bone together, thereby compressing them at the fracture interface in a manner to promote proper mending, while the spiked washer and struts prevent rotational instability of the bone portions.

In orthopedic surgery, where bone fixation pins, screws and other devices are employed, it is normal practice to remove the pin, screws and/or devices after mending of the bone has progressed to a satisfactory extent. However, where implant devices with radially extendable or expandable anchoring mechanisms, including anchoring arms such as I provide, bone regrowth will, in some instances and under certain circumstances, prevent the radially extended anchoring arms or the like from being moved radially inwardly or collapsed when it is desired to remove the devices. When such devices malfunction in the manner set forth above, that is, when they fail to collapse and their removal is impeded, those alternative remedies heretofore available and followed have been to forcibly withdraw the devices or to leave the devices in the bone. The former alternative can only be carried out with considerable destruction to the structure of the bone, thereby resulting in trauma to the bone and prolonging the healing process. If an implant device is left in a bone, it prohibits full regrowth of the bone and presents a continuing location of weakness, irritation or breakdown of the bone.

In accordance with and in furtherance of my invention, the problem of removal of the device is usually obviated and in any event, is greatly alleviated by the provision of an alternate means of withdrawing the radially projecting struts of the anchoring arms 30. To the above end, the implant device 10 of the present invention is provided with or includes an elongate tubular cutting instrument 56 with annular inner and outer ends. The inner annular end of the cutting instrument 56 is, as shown in FIG. 9 of the drawings, formed to establish a serrated cutting edge 58. The instrument 56 is substantially equal in inside diametric extent with the major outside diametric extent of the sleeve 22 and is engageable about the sleeve for free longitudinal and rotary movement relative thereto. When the instrument 56 is slidably engaged about and moved axially inward relative to the sleeve 22 and into engagement with the inner ends of the struts 32 adjacent the base portions of the arms 30, the cutting instrument is rotated so that the cutting edge 58 cuts through the base portions of the arms at the junctions of the struts and severs the struts 32 therefrom. The sleeve 22 with the remainder of the lever arms 30 and the shaft 12 can then be pulled longitudinally outward and withdrawn from the bone, without excessive destruction to the bone. Bone tissue will then reform in the cavity left by the sleeve 22.

In addition to the above and in the preferred embodiment of my invention, an additional means is provided for withdrawing the severed struts 32 from the bone. This added means preferably includes elongate flexible connecting filaments or tow lines 60, best shown in FIGS. 1, 2 and 3 of the drawings. The lines 60 are preferably filamentary stainless steel or nylon lines which are fixed to and extend between the flange 20 on the shaft 12 and the radial outer or free end portions of the struts 32. The lines 60 normally occur outward of the struts and extend radially inward, axially inward of the flange 20 and base portions of the arms so that they will not interfere with or be severed by the cutting instrument when the struts are cut. The lines 60 may be secured in apertures 62 in the flange 20 and in apertures 64 in the struts 32. The lines 60 may be secured by enlarged stops at the ends of the lines which will not pass through the apertures 62 and 64.

When the lines 60 are employed, axial outward movement and withdrawal of the shaft 12 pulls the lines 60. When the shaft 12 is pulled or withdrawn a sufficient distance to draw the lines 60 taut and tension is exerted on the lines 60, the outer ends of the struts are first drawn radially inwardly and axially outwardly in such a manner as to dislodge them from the regrown bone structure and to thereafter pull them longitudinally outward from within the bone.

It is important to note that the force exerted by pulling on the lines 60 acts in notably different directions than the forces which are applied onto and through the struts by the flange 38 on the shaft. In most instances, one or the other of the withdrawal means or mechanisms will free the struts 32 from the structure of the bone and allow the entire implant device to be withdrawn.

For complete understanding of the nature and operation of my new device, I will in the following describe one typical method and procedure of implanting it.

The implant device 10 is particularly suited for fixating bone portions where, as shown in FIG. 10 of the drawings, a fracture of the femoral neck 90 has occurred between the head 72 and the greater trochanter 66, as indicated at 80. When such a fracture occurs, it is extremely important for the bone portions opposite the fracture to be properly fixated and drawn together so as to promote proper mending and so that the patient has quick healing while maintaining proper bone alignment and mobility.

When implanting my device, as with conventional techniques for bringing the bone portions into alignment and abutment, a bore 100 is drilled into the greater trochanter region 66 through the narrow neck 90 leading to the head 72 and into the cancellous material within the head.

Prior to inserting the device, a dummy device is typically inserted into the bore defined in the femur so that the proper size of implant device can be ascertained.

Following removal of the dummy device, the implant device is inserted with the struts 32 thereof collapsed and in juxtaposition along and about the exterior surface of the sleeve 22 as shown in FIG. 3 of the drawings.

When the implant device is installed in the bore in the bone, the struts 32 will not be deployed from their normal position as shown in FIG. 3 of the drawings to their deployed position shown in FIGS. 1, 2 and 10 of the drawings until the nut 36 is tightened. When the nut 36 is tightened, the shaft 12 is drawn longitudinally outwardly relative to the sleeve 22 from the position shown in FIG. 3 of the drawings to the position shown in FIG. 2 of the drawings. Upon outward movement of the shaft 12, the flange 20 thereon pivots the lever arms 34 downwardly about the pivot pins 28 and deploys or pivots the struts 32 radially outwardly, as shown in FIGS. 2 and 10 of the drawings. The nut 36 is then tightened by means of a small socket wrench which fits within the sleeve 22.

Certain orthopedic surgeons may prefer the struts 32 of the arms 30 to be deployed more rapidly. To this end, a biasing means may be interposed between the bearing seat 26' and the nut 36 to normally yieldingly urge the struts to their deployed position shown in FIGS. 1 and 2 of the drawings. Such a biasing means may be a simple coil spring 82, as clearly shown in FIG. 11 of the drawings. Prior to installation of the implant device, the coil spring 82 is not compressed by the nut 36. Rather, the coil spring is allowed to extend and to yieldingly push the nut 36 away from the bearing seat 26' and to thereby pull the shaft 12 longitudinally outwardly. Unless restrained, the spring 82 will normally urge and move the anchoring arms 30 to their deployed position shown in FIG. 2 of the drawings.

During insertion of the device, the surgeon will manually press longitudinally inwardly on the outer securement end 18 of the shank 14 to hold the spring 82 compressed. This causes the flange 38 to collapse the struts 32 to their normal position, as shown in FIG. 3 of the drawings. Once the implant device has been inserted in the bore of the bone, the surgeon will release longitudinal inward pressure on the outer securement end of the shank. Thereupon, the spring 82 is no longer maintained compressed and biases the nut 36 and shaft 12 longitudinally outward relative to the sleeve, causing the struts 32 to pivot outwardly to their deployed position, shown in FIG. 2 of the drawings. The nut 36 is therefter tightened to place the shaft 12 under greater tensile force and to maintain the struts 32 fully radially deployed. Tightening of the nut 36 compresses the spring 82 as illustrated in FIG. 11 of the drawings.

Whether the spring 82 is employed or not, the shaft 12 must be shifted axially outwardly relative to the sleeve 22 from the position shown in FIG. 3 to the position shown in FIG. 2 to move the deployment flange 20 and the operating levers 34 to effect pivoting the struts 32 about the pivot pins 28 and from their normal to their deployed positions. When the struts 32 are fully deployed, they extend into stopped or anchoring engagement with the interior of the cortex of the femoral head 72. Following insertion and/or deployment of the device, smaller bores can be drilled along the femoral shaft corresponding to holes in a related conventional bone plate 70. Cortical compressive fixators 68, such as are fully described in my U.S. Pat. No. 4,409,974, (granted to me in 1983 under my prior name) are deployed through the small bores drilled along the femur and their related holes in the plate 70. As with most conventional bone plates, the bone plate 70 is provided with an annular collar 78 which extends into the reamed bore defined through greater trochanter. The collar 78 is directed toward the neck 90 of the head 72 at which the fracture 80 has occurred. The bone plate 70 is aligned so that the collar 73 fits around the shaft 22 and the cortical compressive fixtures 68 are aligned and secured through the holes in the bone plate and secured in the manner described in U.S. Pat. No. 4,409,974.

Following securing the bone plate 70 to the femoral shaft, nut 46 is tightened putting the shaft 22 in tension and bringing the bone portions toward each other at the interface of the fracture 80.

When the implant device is deployed as depicted in FIG. 10, the sleeve 22 may be immobilized or stopped from rotation relative to the proximal portion of the surrounding femur, which includes the greater trochanter 66, by means of interlocking ribs or projections 84 formed on the opposing abutting surfaces on the axially inwardly disposed side of the nut 46 and the axially outwardly disposed end or surface of the collar 78 on the plate 70.

It will be apparent that when the device that I provide is used in combination with a bone plate, spiked washers such as shown in FIG. 12 of the drawings are not required or used.

Once the greater trochanter 66 bone portion and the head 72 bone portion of the femur, depicted in FIG. 10 of the drawings, have mended sufficiently and it is desired to remove the implant device, to effect removal of the device the nut 46 is disengaged from the sleeve and the cortical compressive fixators 68 are disengaged from the bone plate 70 and the bone plate is removed from engagement in the bore through the femoral neck and head 72. The nut 36 is then threadedly backed off from engagemet with the securement end 18 of the shank 14 of the shaft 12. The shaft 12 can then be pressed and urged axially inwardly to overcome the bias of the spring 82, move the flange 38 and operating levers 34 axially inwardly and cause the struts 32 to pivot to their normal or collapsed positions, as shown in FIG. 3 of the drawings. With the struts 34 thus collapsed and placed in their normal position, the device can be withdrawn from the bone in a clean and non-destructive manner.

Should regrowth of the bony material prevent the struts 32 from fully collapsing to their normal position, thereby preventing safe and non-destructive withdrawal of the device from the bone, the struts 32 are severed from the remainder of the device by using the cutting tool 56 shown in FIG. 9 of the drawings. Once the nut 46 and bone plate 70 have been removed, the cutting tool 56 is engaged about and moved axially inwardly about the sleeve 22 and through the annular space vacated by the collar 78 of the plate 70. When the cutting tool 56 contacts the base portions of the arms 30 adjacent the exterior surface of the sleeve, it is rotated so that its cutting edge 58 cuts the struts 32 free from the remainder of the device. When the struts 32 are severed as noted above, the sleeve 22 can be withdrawn from the bone and then the shaft 12 can be withdrawn separately from the femoral head 72 through the bore in the greater trochanter 66. The severed struts 32 remain attached to the flange 20 on the shaft 12 by the connecting lines or cables 60. The severed struts 32 are pulled from lodgement within the bone upon withdrawal of the shaft 12 and pulling the lines 60.

Referring to FIG. 10 of the drawings, it will be noted that when the implant device is installed to aid in positioning the head 72 relative to the greater trochanter 66 of a femur having a fracture 80 at the neck 90 of the head, the force compressing the two bone portions together is exerted primarily in a longitudinal or axial direction due to the radially and axially inclined disposition of the struts 32 relative to the sleeve Moreover, the ends of the struts 32 act against the hard inner surface of the cortex 74, rather than against the softer, cancellous material 76 confined within it. Furthermore, the struts 32 do not apply lateral force to the neck of the femoral head where the fracture occurs. Rather, the outer end of the struts 32 act within the head against the thickest portion of the cortex 74. The force exerted is primarily a longitudinal compressive force bringing the head portion 72 into abutment with the femoral portion 66 at the interface at the fracture 80. The forces thus exerted minimize the likelihood of damage to the bone and maximize the probability of proper mending in minimum time.

It is to be understood that numerous variations and modifications of my invention are contemplated and can be made or adopted without departing from the broader aspects and spirit of my invention. For example, a much longer version of the implant device of my invention may be employed to properly position the portion of long bones in the arms and legs of human beings where transverse fractures have occurred.

Having described but one typical preferred form and application of my invention, I do not wish to be limited to the specific details herein set forth but wish to reserve to myself any modifications and/or variations that might appear to those skilled in the art and which fall within the scope of the following claims:

Having described my invention, I claim:

1. An implant device for fixating bones in a living body comprising a shaft having an elongate shank with inner deployment and outer securement ends and a lever actuating means at said outer deployment end, an elongate tubular sleeve with inner and outer ends engaged about and shiftable axially of said shank, pivot means defining a plurality of circumferentially spaced axes of rotation about said inner end of the sleeve and radially outwardly offset from said shank, a plurality of anchoring arms each mounted by said pivot means about one of said axes of rotation each arm includes a short lever projecting substantially radially inwardly from its axis of rotation into driving engagement with said actuating means and an elongate strut with inner and outer ends extending longitudinally outward from its axis of rotation and normally in a first position in substantial parallel juxtaposition with said sleeve, said arms are pivotally movable to move the struts to radially outwardly longitudinally inwardly inclined deployed second positions relative to the sleeve upon axial inward shifting of the shaft and actuating means relative to the sleeve; and fastening means releasably holding said shaft and sleeve in set relative longitudinal position and said struts in said second positions.

2. The implant device set forth in claim 1 in which said lever actuating means includes at least one lever engaging flange on said shank.

3. The implant device set forth in claim 1 in which the lever actuating means includes a pair of longitudinally spaced lever arm engaging flanges on said shank between which said lever arms are engaged so that upon longitudinal outward movement of said shaft relative to said sleeve pivots said struts from said first to said second positions.

4. The surgical device set forth in claim 1 wherein the struts of said anchoring arms are arcuate in cross-section and extend about adjacent portions of the outer surface of said sleeve when the struts are in said first position.

5. The implant device set forth in claim 1 wherein the struts of said anchoring arms are arcuate in cross-section and extend about adjacent portions of the outer surface of said sleeve when the struts are in said first position, said device further includes elongate flexible connectors extending radially and longitudinally about the inner end of the shaft and the struts and fixed to said shaft and to said struts at positions spaced from the inner end thereof.

6. The implant device set forth in claim 1 wherein the struts of said anchoring arms are arcuate in cross-section and extend about adjacent portions of the outer surface of said sleeve when the struts are in said first position, said device further includes elongate flexible connectors at positions spaced from the inner end thereof, and an elongate tubular cutting instrument with inner and outer ends removably slidably and rotatably engaged about said sleeve, said instrument has an annular cutting edge at its inner end engageable with the inner ends of the struts, said instrument cuts the struts from their related arms upon axial inward movement and rotation of said instrument relative to the sleeve.

7. The implant device set forth in claim 1 which further includes spring means at and between the outer ends of the shaft and sleeve normally yieldingly urging the shaft axially outward relative to the sleeve and moving said struts to said second positions, manually accessible means at the outer ends of sid shaft and sleeve to disable said spring means and allow for axial inward movement of the shaft and movement of the arms from their first to their second positions.

8. The implant device set forth in claim 1 in which said outer ends of said sleeve and the shank of said shaft are externally threaded, the outer end portion portions of said sleeve defines an axially outwardly disposed annular seat said fastening means includes a first nut threaddedly engaged on the outer end of said shank and in bearing engagement with said seat, a second nut is threaddedly engaged on the outer end of said sleeve and has an axially inwardly disposed surface to oppose and exert axially inwardly disposed force upon a bone in which the device is engaged.

9. The implant device set forth in claim 1 in which said outer ends of said sleeve and the shank of said shaft are externally threaded, the outer end portion of said sleeve is made to define an axially outwardly disposed annular seat, said fastening means includes a first nut threaddedly enged on the outer end of said shank and in bearing engagement with said seat, a second nut is threaddedly engaged on the outer end of said sleeve and has an axially inwardly disposed surface to oppose and exert axially inwardly disposed force upon a bone in which the device is engaged, said fastening means next includes a part to engage a related bone to prevent rotation of the sleeve relative to the bone.

10. The implant device set forth in claim 1 which further includes means in adjacent portions of and preventing relative rotation between said shaft and said sleeve and including a longitudinally extending groove in one of said adjacent portions and a key on the other of said adjacent portions and engaged in said groove.

11. An implant device for in vivo implantation to fixate living bones comprising an elongate shaft having a shank with inner deployment and outer securement ends and a radially projecting flange means at its inner deployment end, an elongate tubular sleeve slidably engaged about said shank and having inner deployment and outer securement ends, said sleeve has pivot means at its inner end defining a plurality of circumferentially spaced axes of rotation, said axes of rotation are normal to and radially outwardly offset from the axis of said shank, a plurality of anchor arms carried by said pivot means about said axes of rotation, each arm has an elongate strut with inner and outer ends extending outward from said pivot means and an operating lever projecting from said pivot means into engagement with said flange means, said struts are movable between undeployed first positions adjacent to and parallel with the sleeve and radially longitudinally outwardly inclined deployed second positions upon axial outward movement of the shank and flange means relative to said sleeve, and fastening means at said outer securement ends of said shaft and sleeve releasably fastening said shaft and sleeve against relative axial shifting.

12. The implant device set forth in claim 11 wherein said struts of said arms are arcuate in cross-section and extend about adjacent portions of said sleeve when the struts are in their first position.

13. The implant device set forth in claim 11 which further includes elongate flexible connector lines extending radially out from the upper end of the shaft and longitudinally of the struts and fixed to and extending between the struts and said shaft.

14. The surgical implant device set forth in claim 11 which further includes means preventing said shaft from rotating relative to said sleeve and including longitudinally shiftable non-relatively rotatable interengaged parts on said shaft and sleeve.

15. The implant device set forth in claim 11 wherein said sleeve has an axially outwardly disposed annular seat at its outer end and said shank is externally threaded at its outer end, said fastening means includes a nut engaged on the outer end of the shank and engaging said seat.

16. The implant device set forth in claim 11 wherein said sleeve has an axially outwardly disposed annular seat at its outer end and said shank is externally threaded at its outer end, said fastening means includes a nut engaged on the outer end of the shank and engaging said seat, the outer end of said sleeve is externally threaded and said fastening means further includes a bone engaging part threadedly engaged on and projecting radially outward from said sleeve, said part is movable longitudinally outward on the sleeve to exert axially inwardly directed forces onto a bone in which the device is implanted and to exert tensile force onto the sleeve.

* * * * *